(12) United States Patent
Rapoport et al.

(10) Patent No.: US 8,352,385 B2
(45) Date of Patent: Jan. 8, 2013

(54) LOW-POWER ANALOG-CIRCUIT ARCHITECTURE FOR DECODING NEURAL SIGNALS

(75) Inventors: Benjamin I. Rapoport, New York, NY (US); Rahul Sarpeshkar, Arlington, MA (US); Woradorn Wattanapanitch, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1181 days.

(21) Appl. No.: 12/127,380

(22) Filed: May 27, 2008

(65) Prior Publication Data

US 2008/0294579 A1 Nov. 27, 2008

Related U.S. Application Data

(60) Provisional application No. 60/940,103, filed on May 25, 2007.

(51) Int. Cl.
*G06F 15/18* (2006.01)
(52) U.S. Cl. ........................................................ 706/12
(58) Field of Classification Search ........................ None
See application file for complete search history.

(56) References Cited

U.S. PATENT DOCUMENTS

2004/0073414 A1    4/2004   Bienenstock et al.

FOREIGN PATENT DOCUMENTS

WO         2007058950       5/2007
WO      WO 2007/058950   *  5/2007

OTHER PUBLICATIONS

Rapoport (Thesis, Massachusetts Institute of Technology, Feb. 5, 2007, pp. 1-122, IDS).*
Eden et al., "Reconstruction of hand movement trajectories from a dynamic ensemble of spiking motor cortical neurons" Conference Proceedings: Annual International Conference of the IEEE Engineering in Medicine and Biology Society. Conference 2004, vol. 6, 2004, pp. 4017-4020.
Rapoport, "Neural prosthetics for paralysis: algorithms and low-power analog architectures for decoding neural signals" Thesis, Massachusetts Institute of Technology, Feb. 5, 2007, pp. 1-122.
Taylor et al., "Direct Cortical Control of 3D Neuroprosthetic Devices" Science, vol. 296, Jun. 7, 2002, pp. 1829-1832.
Wessberg et al., "Real-time prediction of hand trajectory by ensembles of cortical neurons in primates" Letters to Nature, Nature, vol. 408, Nov. 16, 2000, pp. 361-365.
Chapin et al., "Real-time control of a robot arm using simultaneously recorded neurons in the motor cortex" 1999 Nature America Inc. Nature neuroscience vol. 2, No. 7, Jul. 1999, pp. 664-670.
Serruya et al., "Instant neural control of a movement signa" Nature, vol. 416, Mar. 14, 2002, pp. 141-412.
Kennedy et al., "Computer control using human intracortical local field potentials" IEEE Transactions on Neural Systems and Rehabilitation Engineering, vol. 12, No. 3, Sep. 2004, pp. 339-344.

Carmena et al., "Learning to control a brain-machine interface for reaching and grasping by primates" PLos Biology, vol. 1, Issue 2, pp. 001-016.
Wessberg et al., "Optimizing a Linear Algorithm for Real-Time Robotic Control Using Chronic Cortical Ensemble Recordings in Monkeys" 2004 MIT, Journal of Cognitive Neuroscience, 16:6, pp. 1022-1035.
Musallam et al., "Cognitive Control Signals for Neural Prosthetics" Science, vol. 305, Jul. 9, 2004, pp. 258-262.
Zhang et al., "Interpreting Neuronal Population Activity by Reconstruction: Unifie Framework with Application to Hippocampal Place Cell" The American Physiological Society 1998, pp. 1017-1044.
Nenadic et al., "Spike Direction Using the Continuous Wavelet Transform" IEEE Transactions on Biomedical Engineering, vol. 52, No. 1, Jan. 2005, pp. 74-87.
Harrison et al., "A Low Power Integrated Circuit for a Wireless 100-Electrode Neural Recording System" IEEE Journal of Solid State Circuits, vol. 42, No. 1, Jan. 2007, pp. 123-133.
Sarpeshkar et al., "An Ultra-Low-Power Programmable Analog Bionic Ear Processor", IEEE Transactions on Biomedical Engineering, vol. 52, No. 4, Apr. 2005, pp. 711-727.
Sarpeshkar et al., "An Analog Bionic Ear Processor with Zero-Crossing Detection" 2005 IEEE International Solid-State Circuits Conference, pp. 78-79.
O'Halloran et al., "A 10-nW 12-bit Accurate Analog Storage Cell With 10-aA Leakage" IEEE Journal of Solid State Circuits, vol. 39, No. 11, Nov. 2004, pp. 1985-1996.
Sarpeshkar, "Brain Power" IEEE Spectrum, May 2006, pp. 25-29.
O'Halloran et al., "An Analog Storage Cell with 5e/sec Leakage" ISCAS 2006, pp. 557-560.
Sarpeshkar, "Analog Versus Digital: Extrapolating from Electronics to Neurobiology" Neural Computation 10, 1998, pp. 1601-1638.
Mavoori et al., "An autonomous implantable computer for neural recording and stimulation in unrestrained primates" Journal of Neuroscience Methods, 148, 2005, pp. 71-77.
Fetz, "Real-time control of a robotic arm by neuronal ensembles" 1999 Nature America Inc., vol. 2, No. 7, Jul. 1999, pp. 583-584.
Sarpeshkar et al., "A Low-Power Wide-Linear-Range Transconductance Amplifier" Analog Integrated Circuits and Signal Processing, 13, 1997, pp. 123-151.
Haddad et al., "Analog Complex Wavelet Filters" 0-7803-8834-8/05-2005 IEEE, pp. 3287-3290.
Rogers et al., "An Analog VLSI Implementation of a Multi-Scale Spike Detection Algorithm for Extracellular Neural Recordings" 0-7803-8709-1/05 2005, IEEE, pp. v-viii.
Harrison, "A Low-Power Integrated Circuit for Adaptive Detection of Action Potentials in Noisy Signals"Dept. of Electrical and Computer Engineering, University of Utah, pp. 1-4, 2003.

* cited by examiner

*Primary Examiner* — Laura B Goddard
(74) *Attorney, Agent, or Firm* — Gesmer Updegrove LLP

(57) ABSTRACT

A microchip for performing a neural decoding algorithm is provided. The microchip is implemented using ultra-low power electronics. Also, the microchip includes a tunable neural decodable filter implemented using a plurality of amplifiers, a plurality of parameter learning filters, a multiplier, a gain and time-constant biasing circuits; and analog memory. The microchip, in a training mode, learns to perform an optimized translation of a raw neural signal received from a population of cortical neurons into motor control parameters. The optimization being based on a modified gradient descent least square algorithm wherein update for a given parameter in a filter is proportional to an averaged product of an error in the final output that the filter affects and a filtered version of its input. The microchip, in an operational mode, issues commands to controlling a device using learned mappings.

7 Claims, 16 Drawing Sheets

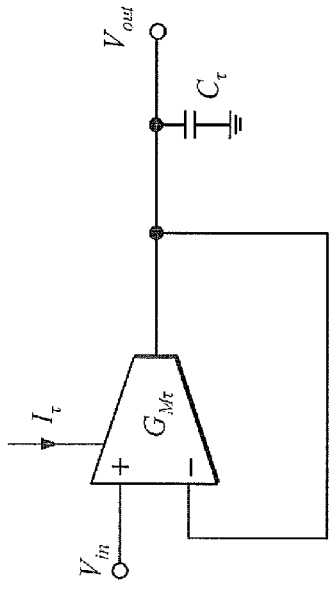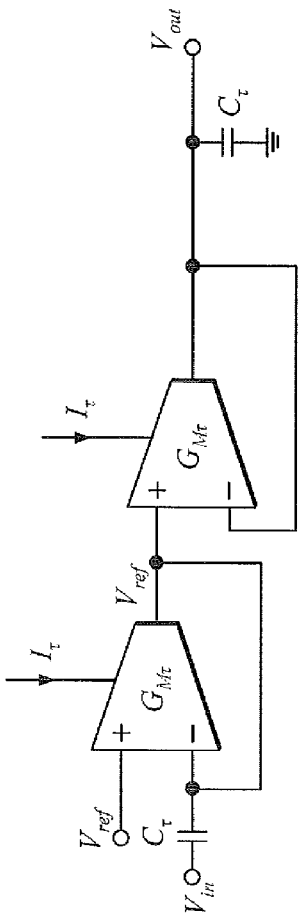
FIG. 6A
FIG. 6B

LOW-POWER ANALOG-CIRCUIT ARCHITECTURE FOR DECODING NEURAL SIGNALS

PRIORITY INFORMATION

This application claims priority from provisional application Ser. No. 60/940,103 filed May 25, 2007, which is incorporated herein by reference in its entirety.

SPONSORSHIP INFORMATION

This invention was made with government support under grant number DGE0645960 awarded by the National Science Foundation. The government has certain rights in this invention.

BACKGROUND OF THE INVENTION

The invention is related to the field of neuromotor prosthetics, and in particular an algorithm for continuous-time linear decoding and learning in neuromotor prosthetics.

In a set of amazing experiments, several groups in the world have now proven that the dream of enabling paralyzed patients to move paralyzed limbs is well within reach. The majority of these experiments have been done in rats or monkeys, although a company, Cyberkinetics Inc., has demonstrated that a paralyzed patient can control a mouse on a computer screen merely by thinking about doing so. However, current neuromotor prosthetics are extremely bulky and power-hungry and are not practical for use in human patients. The system used by Cyberkinetics, for example, requires a full-sized processing computer to be mounted on the wheel chair of the patient and bulky recording electronics to be mounted on the patient's head. Smaller-size portable neural recording has been implemented, but the discrete electronics used require high-power operation and would need further processing to implement an algorithm to decode the intention of the monkey to move. Next-generation neuromotor prosthetics will be small and or fully implanted in the patient's brain, imposing a stringent requirement on power consumption due to the need for small size, long battery life, and minimum heat dissipation in the brain and skull. Power-efficient algorithm and electronic design can make portability and chronic usage of neuromotor prosthetics in real patients a reality.

One major concern in the design of a neuromotor prosthetic system is the power consumption in the digitization of raw neural signals (at 10 bit precision and 20 kHz bandwidth) and in the wireless communication circuitry for transmitting digitized neural data out of the brain (20 $Mbs^{-1}$ for 100 neural channels). The power costs of both the wireless communication and raw neural signal digitization can be significantly reduced if an analog network is used to preprocess the information such that low-precision, low bandwidth information is communicated out of the brain, thus saving power in digitization, communication, and digital post-processing of the communicated information. For the typically low bandwidths and precisions needed at the output of a neuromotor prosthetic (a 10 ms response time on the actuator controls at best, 8 bits of precision, and 3 motor output dimensions), an analog network that is capable of computing 3 motor outputs from 100 analog neural signals can enable a significant reduction in the communicated data bandwidth from about 20 $Mbs^{-1}$ to 2.4 $kbs^{-1}$ and a significant reduction in the overall system power.

As an example, analog preprocessing could enable more than an order of magnitude reduction in power in cochlear-implant processors by enabling digitization of output spectral information for driving electrodes rather than immediate digitization and digital signal processing of raw sound data from a microphone. That processor was also programmable with 373 bits enabling a change of 86 chip parameters. It was robust to power-supply-noise at RF frequencies and temperature variations because of the use of noise-robust biasing techniques.

The use of an analog network for preprocessing to achieve drastic data reduction is beneficial in lowering power in other schemes that have been implemented as well: For example, systems with multichannel wireless telemetry of threshold spikes could be adapted to reduce their power requirements by lowering their digitization and telemetry costs with a scheme such as ours for prosthetic applications. Analog processing is particularly advantageous in slow-and-parallel applications like neuromotor prosthetics where the final output bandwidth and needed precision for the task are relatively modest and involve significant data reduction. In such applications, the noise and offset in an analog system may be managed efficiently to preserve the needed output precision.

A variety of decoding techniques have been developed and implemented successfully in rodents, monkeys, and humans. Major commonalities among the decoding methods employed in these systems have been reviewed in the literature, and include two primary strategies: adaptive linear filtering and probabilistic methods. Thus far, all of these techniques have been proposed for discrete-time digital implementations. In spite of dramatic preliminary successes reported in the field of neuromotor prosthetics, all existing systems accomplish neural decoding through the use of massive amounts of signal-processing hardware and digital post processing.

A highly sophisticated decoding algorithm is not necessarily more beneficial in the long run because the brain is adept at learning and compensating for errors in the decoding algorithm if sensory feedback is present. Learning is nevertheless important in the decoding algorithm to ensure that performance does not degrade over time due to the loss of certain neural signals via electrode degradation which can be compensated for by the brain by using other functional neural signals in the array, and to adapt to the slow variability of the recordings.

SUMMARY OF THE INVENTION

According to one aspect of the invention, there is provided a method for performing the operations of a neural decoding system. The method includes in a training mode, learning to perform an optimized translation of a raw neural signal received from a population of cortical neurons into motor control parameters. The optimization being based on a modified gradient descent least square algorithm wherein update for a given parameter in a filter is proportional to an averaged product of an error in the final output that the filter affects and a filtered version of its input. Also, the method includes in an operational mode, controlling a device using learned mappings in the training mode.

According to another aspect of the invention, there is provided a microchip for performing a neural decoding algorithm. The microchip is implemented using ultra-low power electronics. Also, the microchip includes a tunable neural decodable filter implemented using a plurality of amplifiers, a plurality of parameter learning filters, a multiplier, a gain and time-constant biasing circuits; and analog memory. The microchip, in a training mode, learns to perform an optimized translation of a raw neural signal received from a population of cortical neurons into motor control parameters. The optimization being based on a modified gradient descent least square algorithm wherein update for a given parameter in a filter is proportional to an averaged product of an error in the final output that the filter affects and a filtered version of its input. The microchip, in an operational mode, issues commands to controlling a device using learned mappings.

According to another aspect of the invention, there is provided an ultra-low power microchip implantable inside a skull. The microchip implements a neural decoding algorithm. The microchip includes, in a training mode, learning to perform an optimized translation of a raw neural signal received from a population of cortical neurons into motor control parameters, the optimization being performed according to the following learning rule:

$$-(\overline{\nabla} E_i)_{f,k} = -\int_{t-\sigma}^{t} 2[e_i(u)] \times \left(-\frac{\partial W_f(u)}{\partial p_{f,k}} * N_f(u)\right) du,$$

where $\overline{\nabla} E_i$ is a gradient, $e_i(u)$ is the error at time u, $N_f(u)$ is an N-dimensional vector containing neural signal data at time u, $W_f(u)$ is an impulse response kernel corresponding to a filter applied to $N_f(u)$, and $$\frac{\partial W_f(u)}{\partial p_{f,k}}$$

is a convolution kernel. The microchip, in an operational mode, issues commands to controlling a prosthesis using learned mappings.

According to another aspect of the invention, there is provided a method for performing the operations of neural decoding system. The method includes, in a training mode, learning to optimize a mapping from raw neural signals received from a population of neurons. Also, the method includes, in an operational mode, using the mapping optimized in step mentioned above.

BRIEF DESCRIPTION OF THE DRAWINGS

FIGS. 6A-6B are schematics diagrams illustrating parameter learning filters formed in accordance with the invention;

DETAILED DESCRIPTION OF THE INVENTION

The invention involves a design to achieve continuous-time neural decoding in a miniature, implantable, ultra-low-power context. The invention is based on analog circuitry that implements a real-time, adaptive linear filtering algorithm and least-squares estimation to map neural signal inputs onto motor command outputs. Provided a desired, or target motor control output, a system of analog circuitry is employed to automatically tune all the gains and time constants for the entire neural decoding matrix in real time while neural inputs are present. Once the decoding filters are trained, the parameters are stored in a system of analog-memory elements or as parameters of a DAC, ready to be used for decoding the movement intentions of a paralyzed patient.

Figure 1:
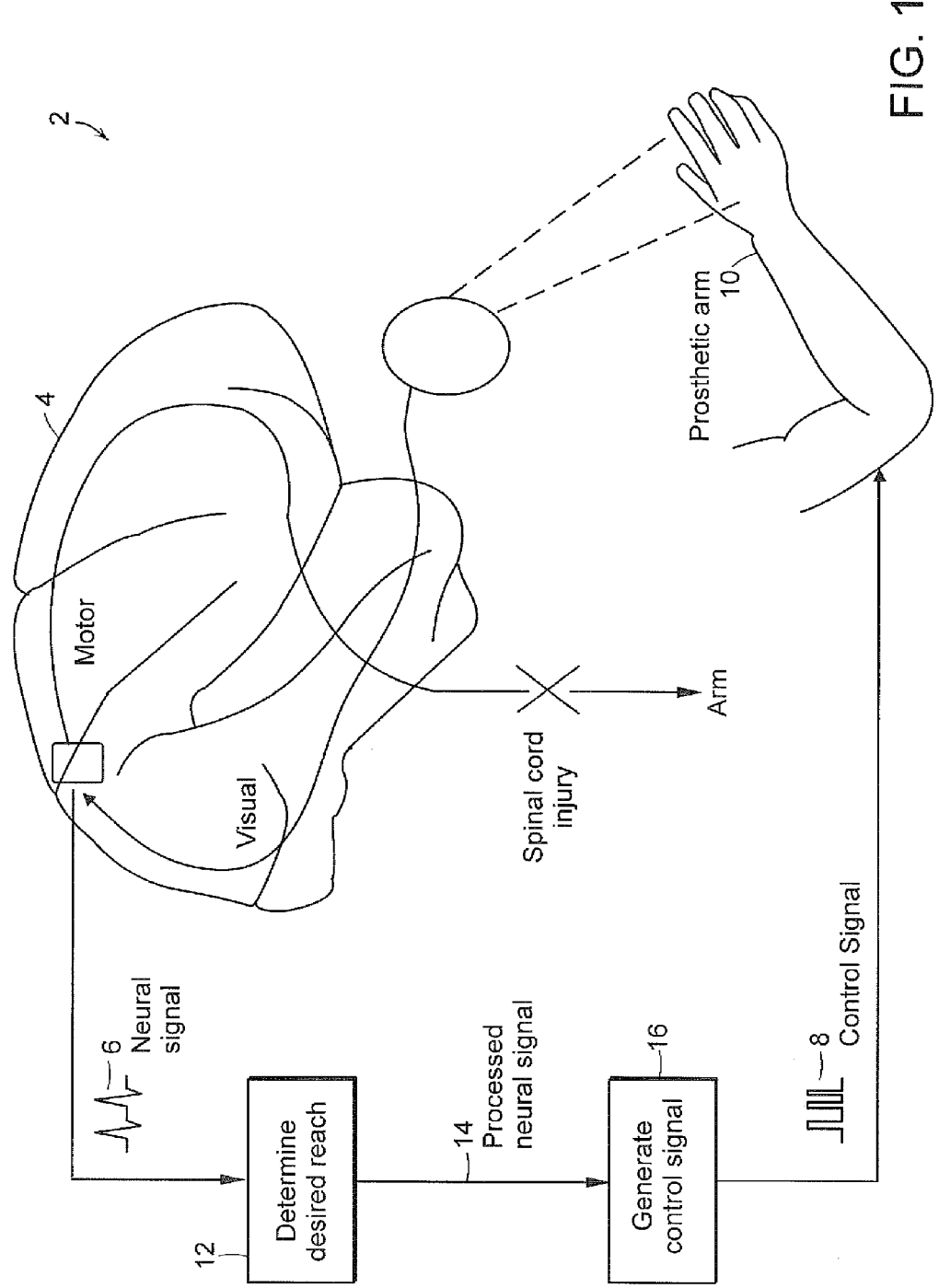
FIG. 1 is a schematic diagram illustrating a prosthetic arm system.

The function of neural decoding is to map neural signals onto the motor commands to which those signals correspond. In a neuromotor prosthetic system 2, such as the example system shown in FIG. 1, the neural signals 6 are obtained from electrode interfaces 12 connected on the brain 4 with populations of cortical neurons. The decoding system 16 must transform these raw data 14 into the control signals 8 for manipulation of a prosthetic limb 10. Such a system 2 typically has two modes of operation: A training mode in which it learns the mapping it must implement, and an operational mode in which it uses the learned mapping to control a prosthesis. The mathematical foundations of a modified gradient descent least-squares algorithm is presented that operates in real time and automatically learns how to perform an optimized translation of raw neural signals into motor control parameters.

The gradient descent least-squares algorithm is a method for optimizing a linear transformation of the form $$M(t) = \int_0^t W(t-u) \cdot N(u) du \qquad \text{Eq. 1}$$

where N(t) is an n-dimensional vector containing the neural signal data at time u (which may consist of firing rates, analog values, or local field potentials), M(t) is an m-dimensional vector containing the motor output parameters generated at time t (which may include of limb positions, motor velocities, cursor positions, other dynamic variables describing limb motion), and W(t) is an m×n weighting matrix kernel that is convolved with N(t) to generate M(t). A desired $M_{target}$(t) is used to generate N(t) by adopting W(t) through the least squares error over some integration interval, δ. The error at time t is the vector $$e(t) = M_{target}(t) - \left(M(t) = \int_0^t W(t-u) \cdot N(u) du\right) \qquad \text{Eq. 2}$$

Optimizing the kernel in a least-squares sense corresponds to minimizing $$E = \sum_{i=1}^{m} \int_{t-\sigma}^{t} |e_i(u)|^2 du \quad \text{Eq. 3}$$

the quantity over a time window set by σ. Under the assumption that each motor output contributes independently to the least-squares error and is determined by an independent set of parameters, one can optimize the system by minimizing the least-squares error of each motor output separately. For convenience, the convolution of two arbitrary functions $f(t)$ and $g(t)$ is defined as $$f(t) * g(t) = \int_0^t f(t-u) \cdot g(u) du. \quad \text{Eq. 4}$$

Therefore, a given motor control output, $M_i(t)$, is equal to $W_{i,1}(t)*N_1(t)+W_{i,2}(t)*N_2(t)+ \ldots +W_{i,n}(t)*N_n(t)$, where each of the $W_{ij}(t)$ is an impulse-response kernel corresponding to a filter applied to $N_j(t)$. The error-squared term for a given motor output $M_i(t)$, n neuronal inputs, and k filter parameters in each impulse-response kernel is given by Eq. 5:

$$e_i(t) = \int_{t-\sigma}^{t} \left[ M_{target,i}(u) - \left( \sum_{j=1}^{n} W_j(u) * N_j(n) \right) \right]^2 du. \quad \text{Eq. 5}$$

Gradient descent requires that one slowly and gently alter the parameters of the W kernels in a direction that is against the gradient of this error function in the n×k dimensional space of its parameters. That is, if one would like to adapt the $k^{th}$ parameter of the $Wf$ filter, $p_{f,k}$, then one can change this parameter with a term proportional to where the gradient term is given explicitly in Eq. 6.

$$-(\nabla E_i)_{f,k} = -\int_{t-\sigma}^{t} 2 \left[ M_{target,i}(u) - \left( \sum_{j=1}^{n} W_j(u) * N_j(n) \right) \right] \times \quad \text{Eq. 6}$$

$$\left( -\frac{\partial W_f(u)}{\partial p_{f,k}} * N_f(u) \right) du.$$

Substituting Eq. 2 into Eq. 6 yields Eq. 7:

$$-(\nabla E_i)_{f,k} = -\int_{t-\sigma}^{t} 2[e_i(u)] \times \left( -\frac{\partial W_f(u)}{\partial p_{f,k}} * N_f(u) \right) du \quad \text{Eq. 7}$$

While this learning rule may appear to be rather complicated, it is actually a very simple modification of the well-known "delta rule" in neural-network theory: It says that the update for a given parameter in a filter is proportional to the averaged product of the error in the final output that the filter affects and a filtered version of its input. The filtered version of the input is generated by a convolution kernel $$\frac{\partial W_f(u)}{\partial p_{f,k}},$$

which is different for each parameter of the filter, but the error term is the same for every parameter in the filter. In fact, the error term is the same for the parameters of all the filters that affect a given motor output. The average is taken over a time interval σ.

Figure 2:
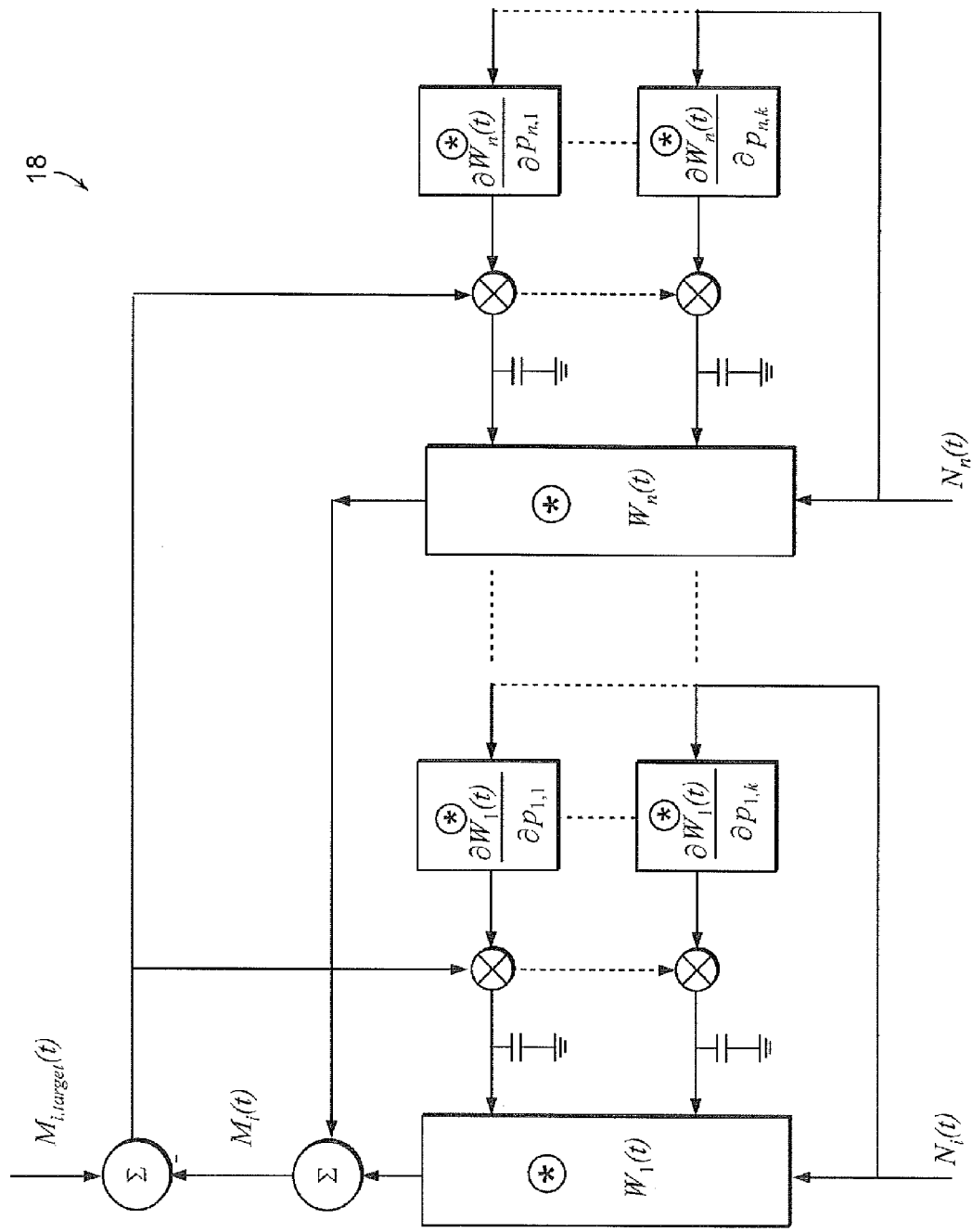
FIG. 2 is a block diagram of the inventive analog architecture for linear decoding and learning.

The invention includes an analog architecture 18, schematized in the block diagram shown in FIG. 2 that implements this strategy. The averaged product is implemented by using the outputs of the product blocks to alter the voltages on the capacitors that store the parameters. The values on the capacitors are changed via exponentially weighted averaging with the impulse response of a lowpass filter or time-windowed averaging between read-and-write cycles on an analog memory.

Figure 3:
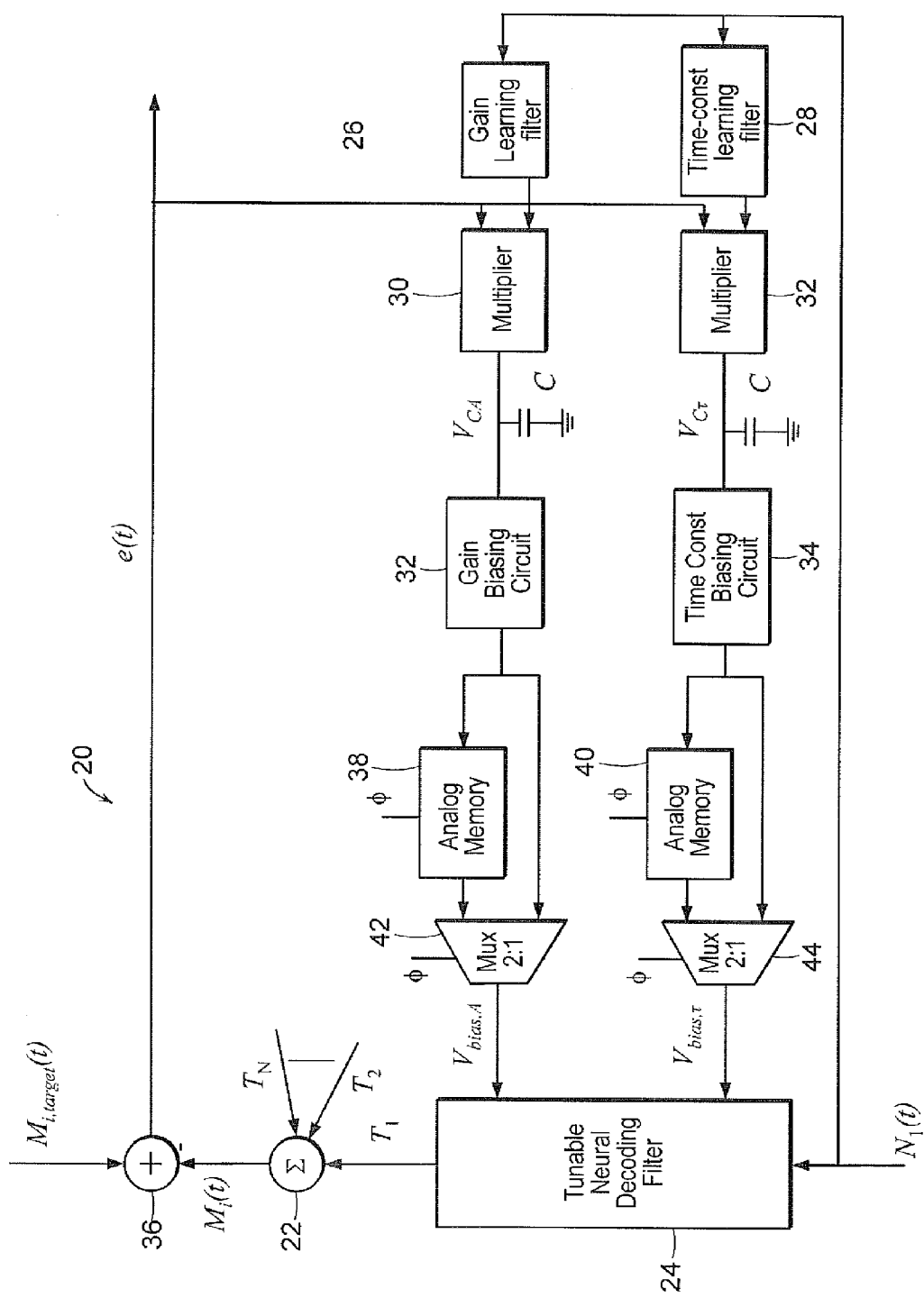
FIG. 3 is a block diagram of a system that implements the architecture of FIG. 2 with circuit building blocks.

The analog architecture of FIG. 2 uses transistor circuit models from a standard 0.18 μm CMOS process. The block diagram for the entire system 20 is shown in FIG. 3. Standard analog circuit blocks such as Gm-C filters, Gilbert multipliers and translinear circuits are used to implement the function shown in FIG. 3. The implementation is a proof-of-concept example. Low-frequency operation (100 Hz bandwidth is more than adequate for motor prosthetics) enables ultra-low-power operation by allowing the subthreshold bias current for each circuit building block to be very low (1 to 20 nA). A first-order lowpass filter with two filter parameters, A and r, is used for each tunable neural decoding filter for simplicity. It is easy to generalize higher-order filters with more parameters by modifying the FIG. 3 schematic to correspond to the filter order and number of parameters of FIG. 2.

Figure 4A:
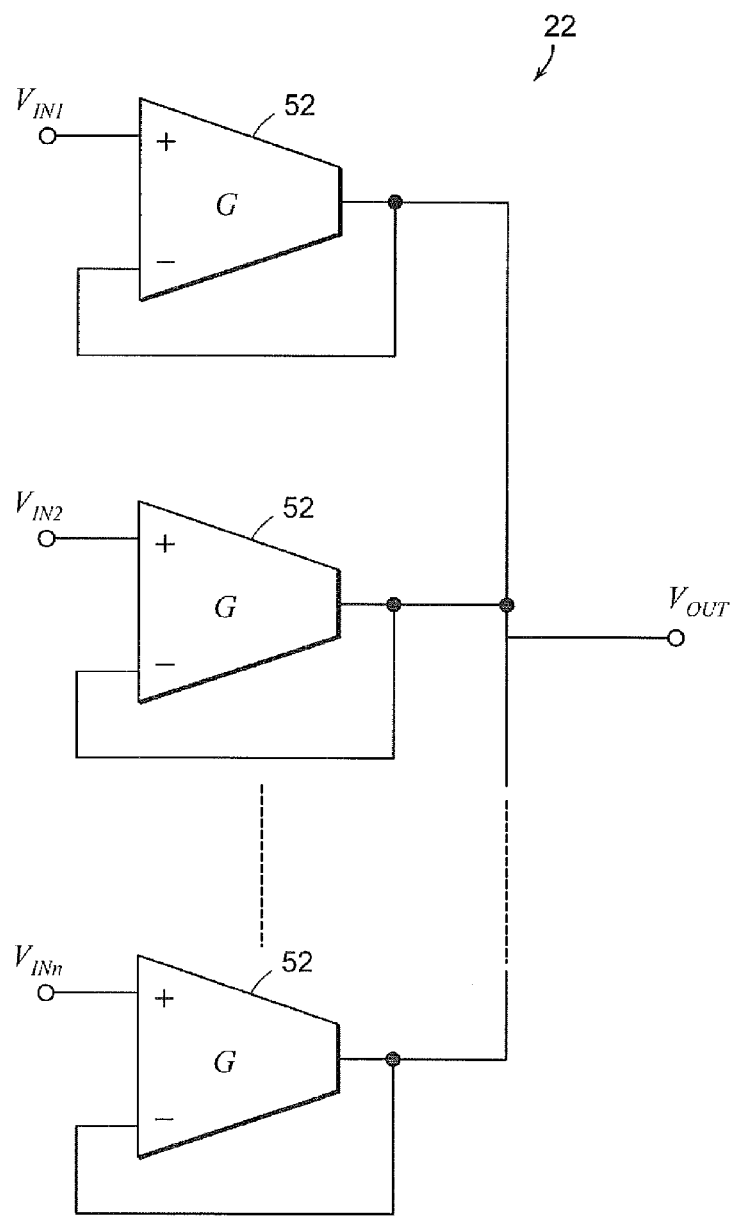
FIGS. 4A-4B are schematic diagrams of an adder and subtracter formed in accordance with the invention.

The bias voltages $V_{bias,A}$ and $V_{bias,\tau}$ in FIG. 3 set the gain and time constant of the tunable decoding first-order lowpass filter 24, respectively. The digital control signal $\phi$ is used to control whether the system is in the learning phase or the decoding phase such that the bias voltages do not or do get inputs from the analog memory respectively. An adder 22 combines the outputs of all the channels into a motor control signal Mi(t). The adder 22 is implemented using the follower-aggregation circuit, as shown in FIG. 4A. The inverting input node of the amplifiers 52 are coupled to output signal $V_{out}$ and the non-inverting input node of the amplifiers 52 are coupled to their respective input signals $V_{1n}$-$V_{3n}$.

Figure 4B:
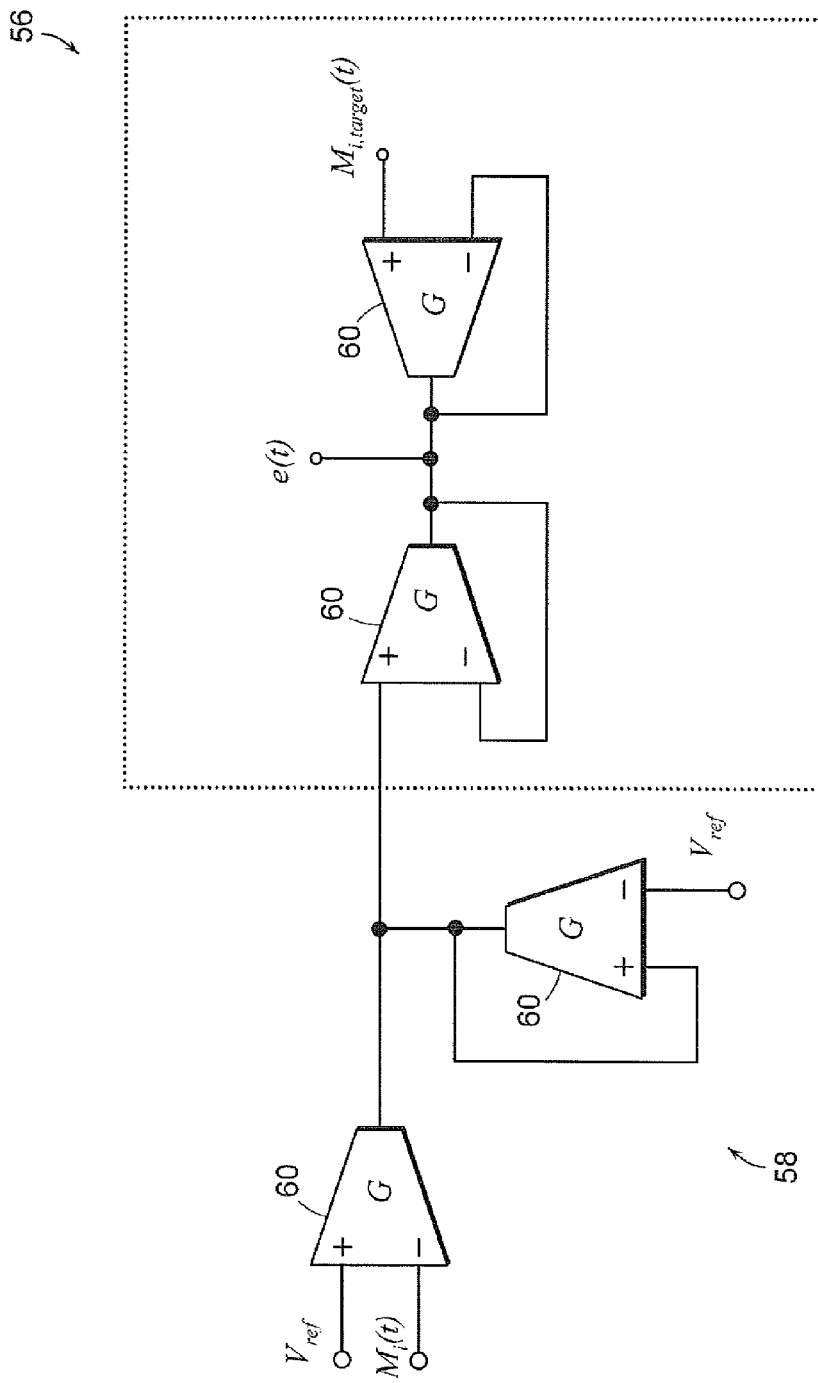

The motor control signal $M_i(t)$ is subtracted from the motor target signal $M_{target}(t)$ by a subtracter 36, implemented with an inverting amplifier 58 and an adder 56, to create the error signal e(t), as shown in FIG. 4B. The error signal e(t) is multiplied by the output of either the gain-learning or time-constant-learning filters 26, 28 using the Gilbert analog multipliers 30. The linear capacitors C at the output of the analog multipliers 30 integrate the output currents to form the voltage signals, $V_{CA}$ and $V_{C\tau}$ which are used to set $V_{bias,A}$ and $V_{bias,\tau}$ via the gain-biasing or time-constant-biasing circuits 32, 34 respectively. Both the adder 56 and inverting amplifier 58 use amplifier 60 to form their respective structures.

Figure 5:
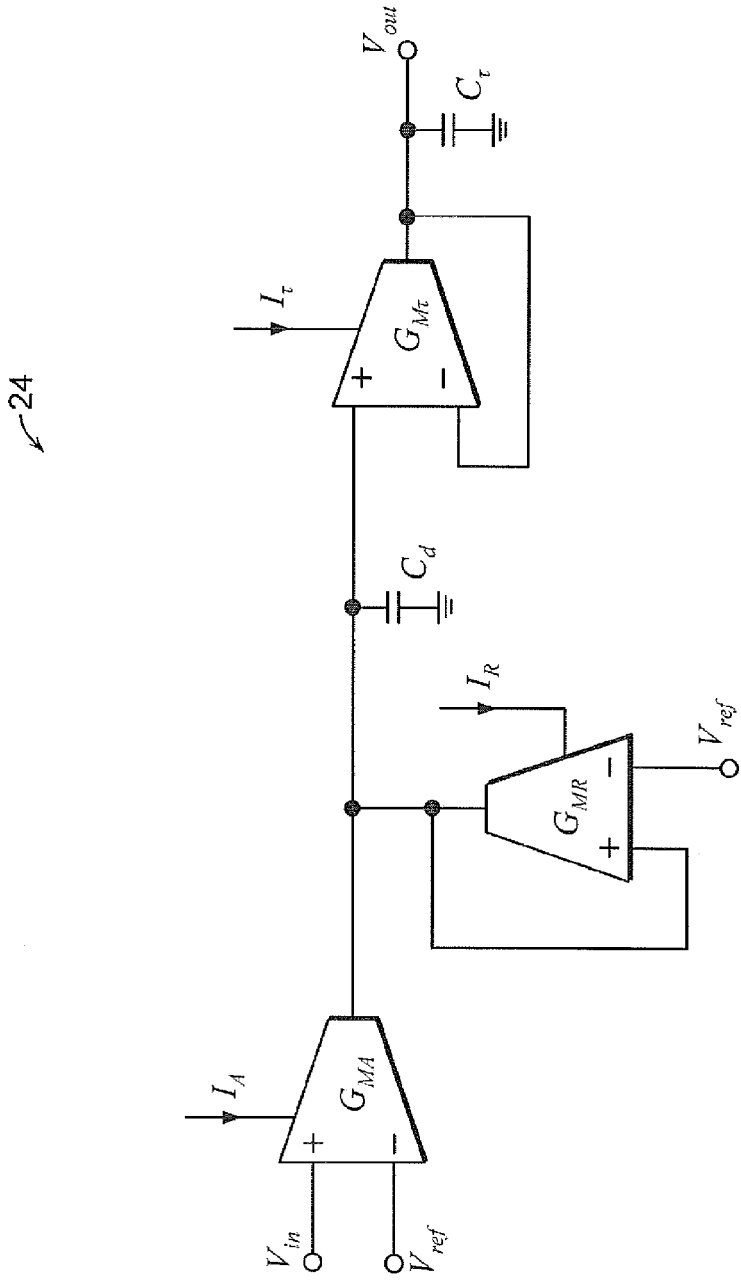
FIG. 5 is a schematic diagram illustrating a tunable neural decoding filter formed in accordance with the invention.

FIG. 5 is a schematic diagram of the tunable neural decoding filter 24. The topology for this tunable filter 24 is a slight modification of the variable gain amplifier (VGA). The filter 24 includes three operational transconductance amplifiers (OTAs). Each OTA is a standard nine-transistor wide output-range operational transconductance amplifier. The first OTA, labeled $G_{MA}$, performs the voltage-to-current conversion. Every transistor in each OTA is operated in the subthreshold regime for energy-efficient operation. The transconductance for the $G_{MA}$ OTA is defined as $G_{MA}=\kappa I_A/U_T$, where κ is the exponential gate coefficient of the MOS transistor with a typical value of 0.7 and $U_T$ is a thermal voltage equal to κT/q, where κ is the Boltzmann constant, T is the temperature, and q is the electron charge. The second transconductance amplifier, labeled $G_{MR}$ is connected in unity-gain follower feedback. The transconductance of the GMR OTA is defined as $G_{MR}=\kappa I_R/U_T$. The capacitor $C_d$ is small and can be neglected but is necessary to provide dominant-pole compensation for the GMR OTA. The third OTA, labeled $G_{M\tau}$, is connected in unity-gain follower feedback configuration with load capacitance $C_\tau$. The values of $G_{MR}$ and $C_\tau$ set the time constant of the tunable decoding filter. Assuming that every transistor has the same value of $\kappa$, one can approximate the transfer function of the tunable decoding filter as $$\frac{V_{out}}{V_{in}}(s) = \frac{I_A}{I_R} \frac{1}{1 + sC_\tau/G_{M\tau}}.$$ Eq. 8

Eq. 8 indicates that one can control the gain of the tunable decoding filter by controlling the current ratio $$\frac{I_A}{I_R}.$$

The time constant of the tunable decoding filter, $\tau=C_\tau/G_{M\tau}$, can be controlled by adjusting the bias current $I_\tau$ to alter $G_{M\tau}$.

As FIG. 2 shows, one needs to have convolution kernels to generate filtered versions of the input during learning. The tunable neural decoding filter used in the implementation is a first-order lowpass filter with an impulse response given by $$W(t) = \frac{A}{\tau} e^{-t/\tau}.$$

For purposes of analysis, however, it is more convenient to work with transfer functions than with impulse responses (i.e., in the Laplace domain rather than in the time domain). Accordingly, one can express $W(t)$ in its equivalent form $$W(s) = \frac{A}{1 + \tau s}.$$

FIG. 3 shows a gain-learning filter 26 and a time-constant-learning filter 28 to compute the error terms for A and $\tau$. Their transfer functions are obtained by taking the partial derivatives $\partial W(s)/\partial A$ and $\partial W(s)/\partial \tau$ computed in Eqs. 9 and 10, respectively:

$$W_A(s) = \frac{1}{1 + \tau s}$$ Eq. 9

$$W_\tau(s) = \frac{As}{(1 + \tau s)^2}$$ Eq. 10

According to Eq. 7, one only needs to change the gain and time constant of the tunable decoding filter with a term proportional to the negative gradient of the error function. Thus, one can design parameter-learning filters that have transfer functions proportional to those of Eqs. 9 and 10. Those transfer functions are not required to be implemented exactly. The filter topologies that are used for the learning filters are shown in FIGS. 6A-6B. The transfer functions for the gain-learning filter in FIG. 6A and the time-constant-learning filter in FIG. 6B are $W_A(s)=1/1+\tau s$ and $W_\tau(s)=\tau/(1+\tau s)^2$, respectively, where $\tau=C_\tau/G_{M\tau}$. The OTA $G_{M\tau}$ for these two parameter-learning filters has the same bias current as that of the $G_{M\tau}$ OTA of the tunable decoding filter, so it must also have the same transconductance. As a result, the time constants of all the filters in the entire architecture are updated simultaneously. Note that one needs a sign inversion for the time-constant-learning filter.

Figure 7:
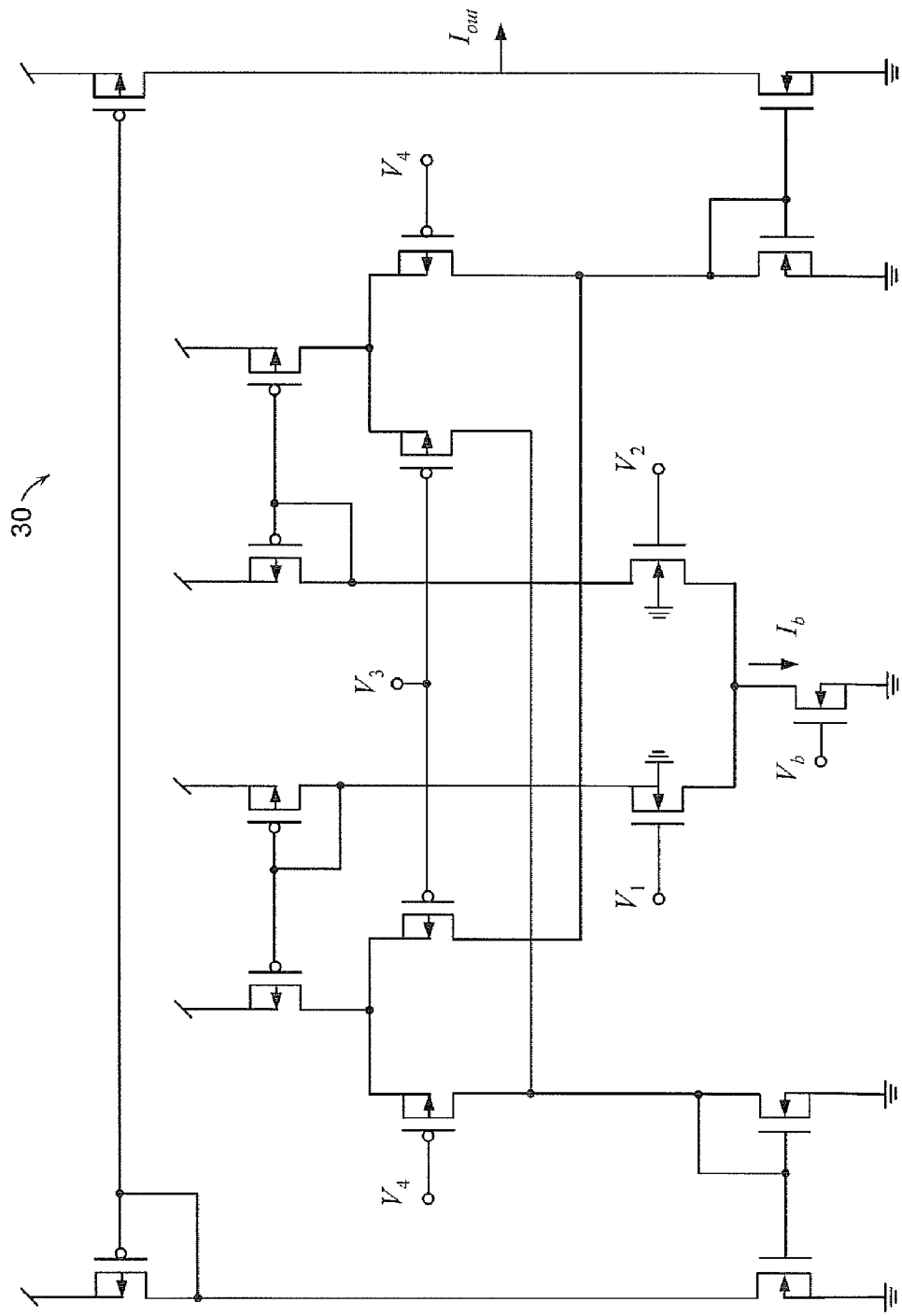
FIG. 7 is a schematic diagram illustrating an analog Gilbert multiplier circuit.

The wide range, four-quadrant Gilbert multiplier 30 is used as shown in FIG. 7 to implement the multiplications required in FIG. 3. The valid input range for V3 and V4 is from ground to a voltage very near the supply voltage. Conversely, the valid input range for V1 and V2 is from the supply voltage down to a voltage very near ground. The input-output characteristic for this multiplier is $I_{out}=I_b \tanh \kappa(V1-V2)/2U_T \tanh \kappa(V3-V4)/2U_T$. In the intended operating region where $V_1 \approx V_2$ and $V_3 \approx V_4$, one can approximate the input-output characteristic as $$I_{out} = I_b \left(\frac{\kappa}{2U_T}\right)^2 (V_1 - V_2)(V_3 - V_4).$$

In this implementation, the multiplier multiplies two voltage inputs, e(t), and a filtered version of the mean firing rate, N(t), and produces an output current that is integrated by the capacitors denoted as C in FIG. 3. To implement non-inverting multiplication, we can set V2 and V4 at a reference DC voltage and feed the two signals into V1 and V3. To obtain the sign inversion required by the time-constant-learning filter 28, one can interchange one signal and its corresponding reference voltage. Since the output of the multiplier is a current, the integration can be implemented using a linear capacitor. Therefore, the capacitor voltages in FIG. 3 can be expressed as $$V_{CA} = \frac{I_b}{C}\left(\frac{\kappa}{2U_T}\right)^2 \int_0^t \left[e(u) \times \left(\frac{\partial W(u)}{\partial A} * N(u)\right)\right] du$$ Eq. 11

$$V_{C\tau} = \frac{I_b}{C}\left(\frac{\kappa}{2U_T}\right)^2 \int_0^t \left[e(u) \times \left(\frac{\partial W(u)}{\partial \tau} * N(u)\right)\right] du$$ Eq. 12

Notice the similarities among Eqs. 11, 12 and 7. Small adjustments of magnitude $\Delta V_{CA}(t)$ and $\Delta V_{C\tau}(t)$ are continuously made to the capacitor voltages, where the magnitudes of these adjustments are given by (13) and (14), respectively:

$$\Delta V_{CA}(t) = \lim_{\sigma \to 0} \frac{I_b}{C}\left(\frac{\kappa}{2U_T}\right)^2 \int_{t-\sigma}^t \left[e(u) \times \left(\frac{\partial W(u)}{\partial A} * N(u)\right)\right] du$$ Eq. 13

$$\Delta V_{C\tau}(t) = \lim_{\sigma \to 0} \frac{I_b}{C}\left(\frac{\kappa}{2U_T}\right)^2 \int_{t-\sigma}^t \left[e(u) \times \left(\frac{\partial W(u)}{\partial \tau} * N(u)\right)\right] du$$ Eq. 14

It follows from Eqs. 13 and 14 that the increments in the capacitor voltages $\Delta V_{CA}(t)$ and $\Delta V_{C\tau}(t)$ have the same form as the expression for the gradient given in Eq. 7. These increments can therefore be used to modify the gain and time constant of the tunable decoding filter, respectively.

Figure 8A:
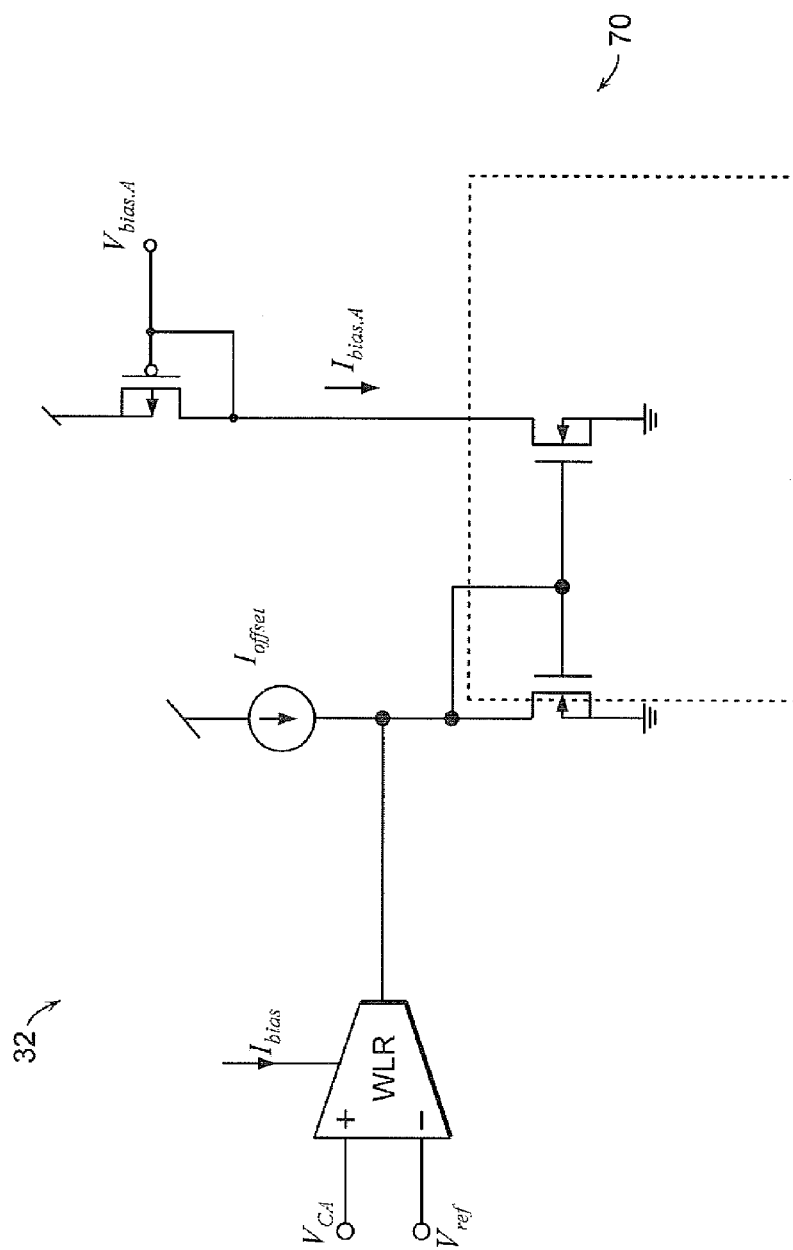
FIGS. 8A-8B are schematics diagrams illustrating biasing circuits formed in accordance with invention.

Changes in the integration capacitor voltages represent adjustments of the gain and time constant of the decoding filter 26, 28. Since the gain of the tunable decoding filters 26, 28 are proportional to the bias current $I_A$ in the $G_{MA}$ OTA shown in FIG. 5, one can change $I_A$ in proportion to the change in capacitor voltage $V_{CA}$ by converting the capacitor voltage $V_{CA}$ into a current that is proportional to $V_{CA}$ and then use a mirror copy of this current to bias the $G_{MA}$ OTA in the tunable decoding filter. The schematic of the gain-biasing circuit 32 is shown in FIG. 8A. To convert $V_{CA}$ into a proportionally scaled current, a wide-linear-range transconductance amplifier (WLR) is used. To ensure that the current flowing into the input of the NMOS current mirror 70 is always positive, one can add an offset current $I_{offset}$ equal to $I_{bias}$ at the output of the WLR.

Figure 8B:
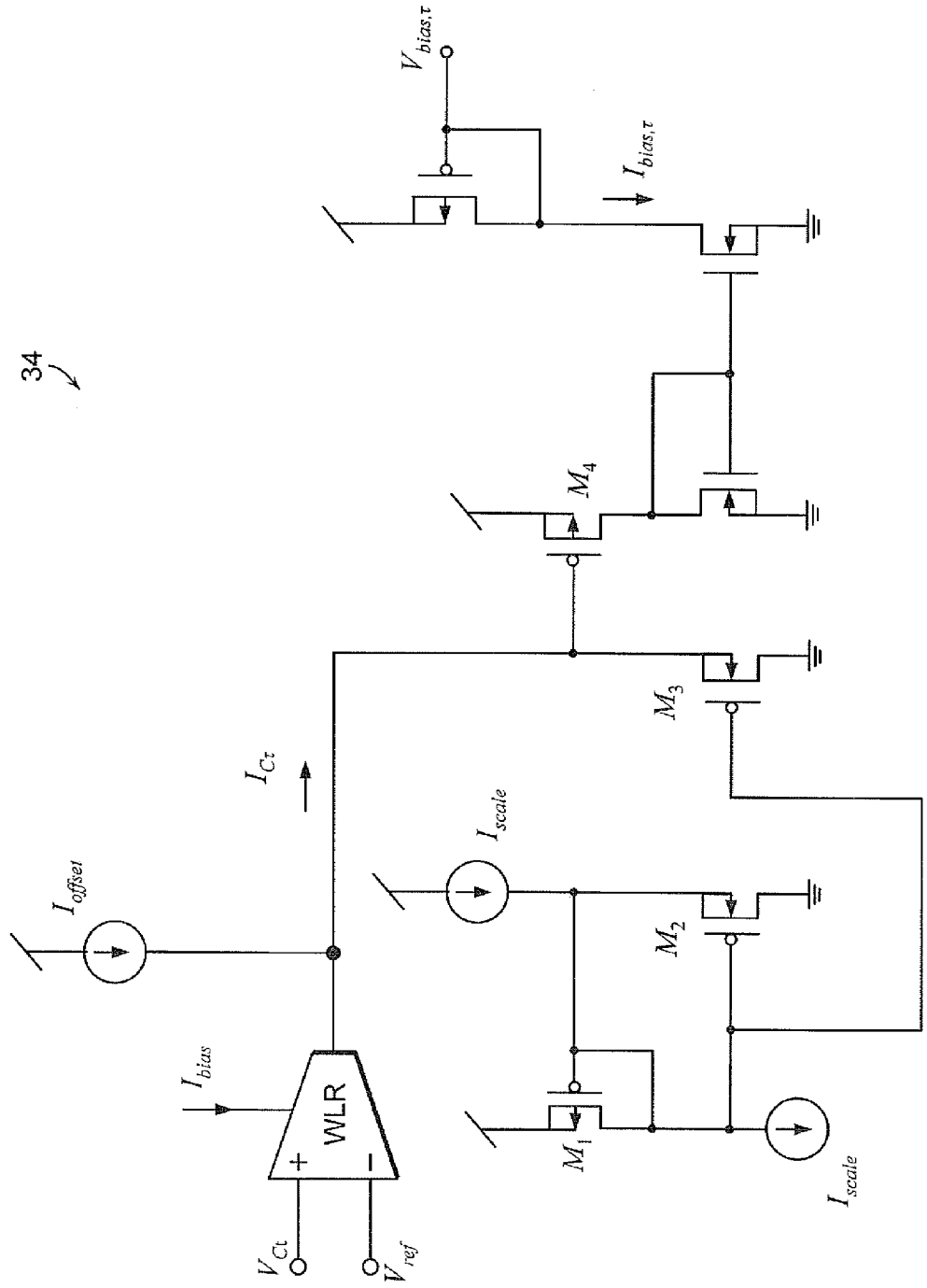

Changing the time constant of the tunable decoding filter 24 is slightly more difficult. The time constant of the tunable decoding filter 24 is inversely proportional to the transconductance of $G_{M\tau}$. Therefore, one needs to set the bias current in the $G_{M\tau}$ OTA such that it is inversely proportional to $V_{C\tau}$ in FIG. 3. FIG. 8B shows the reciprocation being performed in the time-constant-biasing circuit 34. First, the capacitor voltage $V_{C\tau}$ is converted into current $I_\tau$ in the same manner as in the gain-biasing circuit. The current $I_\tau$ passes into a translinear circuit, formed by subthreshold MOS transistors $M_1$-$M_4$, to take the inverse of $I_\tau$. The relationship between $I_{bias,\tau}$ and $I_{C\tau}$ is $$I_{bias,\tau} = \frac{I_{scale}^2}{I_{C\tau}},$$

assuming that the transistors $M_1$-$M_4$ match well. The bias current $I_\tau$ of the $G_{M\tau}$ OTA of FIG. 5 is a mirror copy of $I_{bias,\tau}$. As a result, the transconductance $G_{M\tau}$, which is proportional to $I_\tau$ is inversely proportional to $V_{C\tau}$ as desired.

The analog memory sample-and-hold circuits 38, 40 are described in detail in and are used to store the bias voltages that set the gain and time constant of the tunable decoding filter 24. The fabricated version of this analog memory in a 0.5-µm CMOS process achieves a 5 electrons/sec leakage on a capacitor due to the use of an ultra-low leakage switch. With a 3.3 V supply, the circuit only loses one bit of voltage accuracy, 11.3 mV on an 8-bit scale, in 3.9 hours. If the system requires frequent calibration, the long hold time and low power consumption of the analog memory aids in conserving power by removing the need for relatively costly digitization of the bias voltage. Digital memory can be used if the system is intended to store the parameters of the tunable decoding filter for intervals longer than several hours. Alternatively, the learning loop can be architected to perform discrete up or down increments of DAC storage registers that determine the $I_A$ and $I_\tau$ currents of FIG. 5.

During the learning phase of the decoding architecture, the analog multiplexers 42, 44 connect the output voltages of the gain and time-constant-biasing circuits 32, 34 to $V_{bias,A}$ and $V_{bias,\tau}$ nodes of the tunable decoding filter. The analog multiplexer is implemented with a CMOS transmission gate. During this time interval, the analog memory is in the sampling phase. At the moment the sampling phase ends, the analog memory holds the instantaneous outputs of the biasing circuits. Each analog multiplexer connects the output of the analog memory to the tunable decoding filter.

Figure 9:
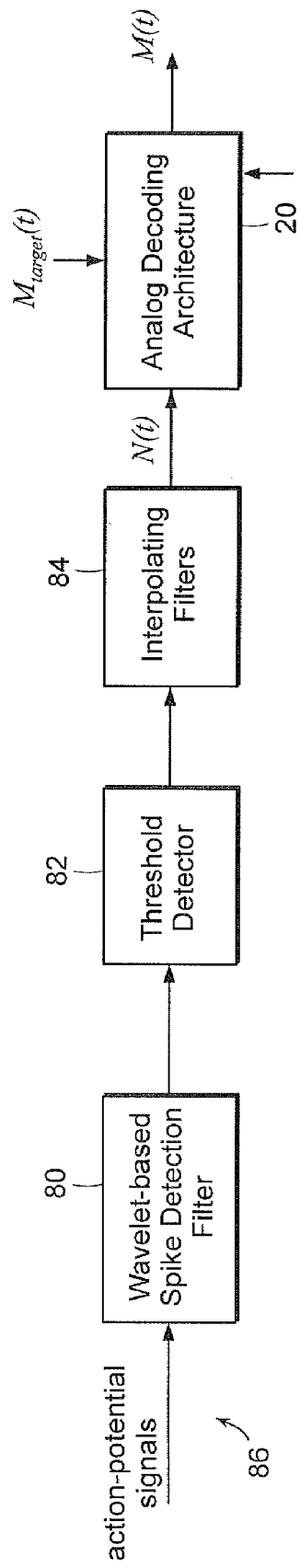
FIG. 9 is a block diagram illustrating a technique to convert action potentials to mean-firing-rate.

The implementation described so far assumes that we have a mean firing rate available as the input for each channel. This section will explain how we can extract mean-firing-rate information from spiking neural signals using ultra-low-power analog circuits. The technique is shown in FIG. 9. First, the neural signals 86 recorded from the electrode array are fed into wavelet-like spike detection filters 80 that have impulse responses similar to the shapes of action potentials to increase the signal-to-noise ratio (SNR). By analyzing large numbers of extracellular waveforms one can find that a filter with a transfer function of the form $$H(s) = \frac{\tau^2 s^2}{(1+\tau s)^2},$$

where $$\tau = \frac{C}{G_m},$$

implemented with standard $G_m$-C filter techniques, is often simple and effective.

Figure 10A:
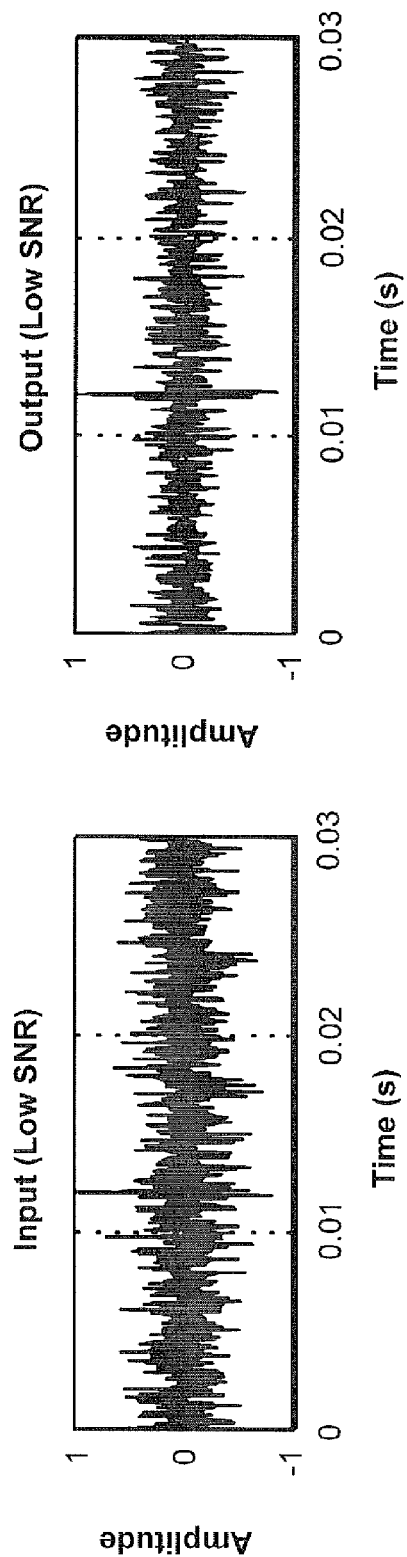
FIGS. 10A-10C are graphs illustrating improvement in SNR after wavelet-like filtering.
Figure 10B:
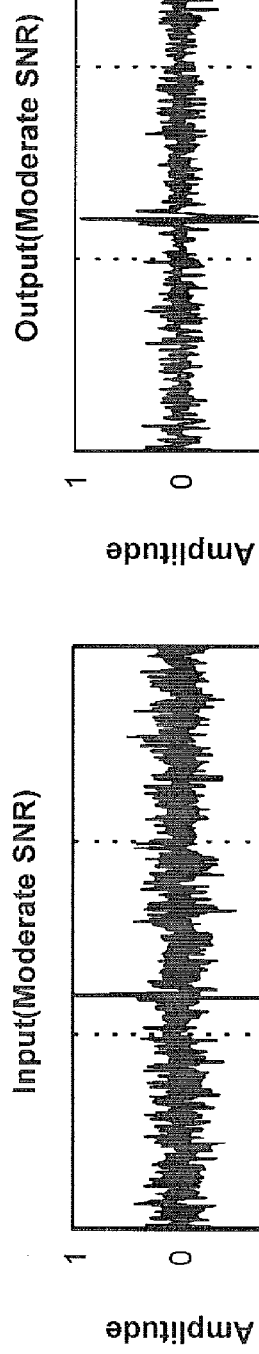
Figure 10C:
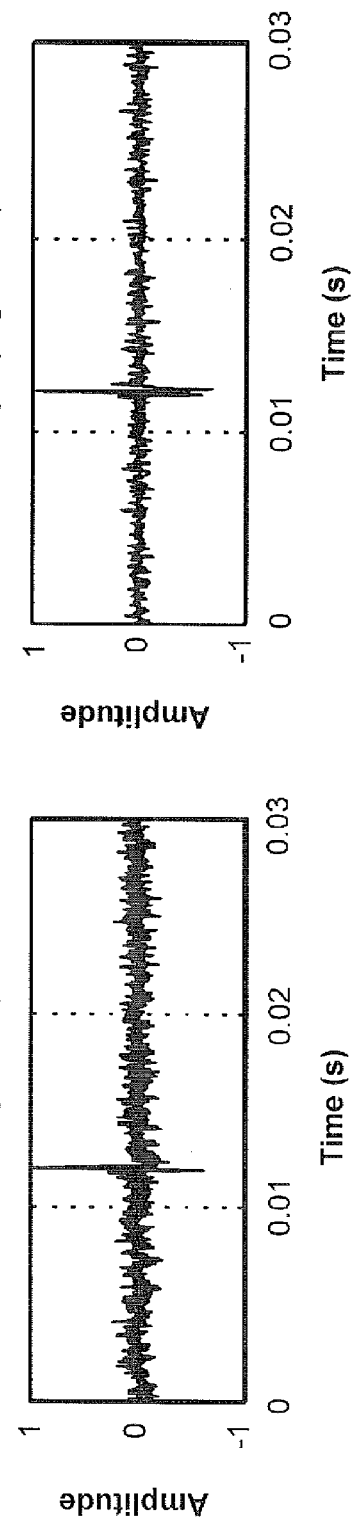

FIGS. 10A-10C shows the improvement in SNR after a noisy recorded neural signal is filtered by the wavelet-like filters 80 described above. Second, the outputs of the wavelet-like spike detection filters 80 are fed to a threshold-detection circuit 82. The output of each threshold detector 82 is a pulse train with each pulse indicating a single spike. The duration of each pulse is on the order of one millisecond. The mean firing rate from the pulse train is extracted by using an interpolation filters 84 composed of three cascaded $G_m$-C lowpass filters. Each filter has a cutoff frequency on the order of 1 Hz. The overall transfer function of the interpolation filter that can be used to extract the mean firing rate is $$H_{int}(s) = \frac{1}{(1+\tau_i s)^3},$$

where $f_c = 1/2\pi\tau_i$ is the cutoff frequency for each lowpass filter. A first-order lowpass filter may also be used as an interpolation filter 84. However the first-order filter produces spiky output due to the form of its impulse response. The higher-order interpolation filter produces smoother output at the expense of circuit complexity. The output of the interpolation filter is provided to the analog decoding architecture 20 of FIG. 2.

In a real prosthetic, digital processing on digitized neural waveforms from each electrode can be used to sequentially select optimal parameters for the analog wavelet filters in each channel, and then downloaded into DAC storage registers that determine the parameters of the wavelet filters. Since these relatively power-hungry operations are only performed every now and then, the power efficiency of analog preprocessing is still preserved.

The invention is tested in two settings. In both settings a ten-channel SPICE simulations is performed of the decoding circuit with transistor models from a standard 0.18 µm CMOS process. In the first simplified setting, one can use a sinusoidal waveform as a mean firing rate input for each channel. In the second setting, one can use experimental spike-timing data to extract the mean firing rate of each channel. The data were collected from posterior parietal cortex in the brain of a monkey in the lab.

A motor target signal is generated by superimposing five sinusoids at frequencies of 250 Hz, 270 Hz, 290 Hz, 310 Hz, and 330 Hz with different phases and amplitudes. One can use a supply voltage of 1 V and provided an offset voltage of 500 mV to all sinusoidal signals. The amplitude of each sinusoid was on the order of a few tens of millivolts. Sinusoids at one of these frequencies were input to each of the ten channels with each frequency being input into two channels. The circuit was then required to adapt the gain A and the time constant τ for each filter to obtain the needed phase shifts and gains in each channel to track the target motor signal.

Figure 11A:
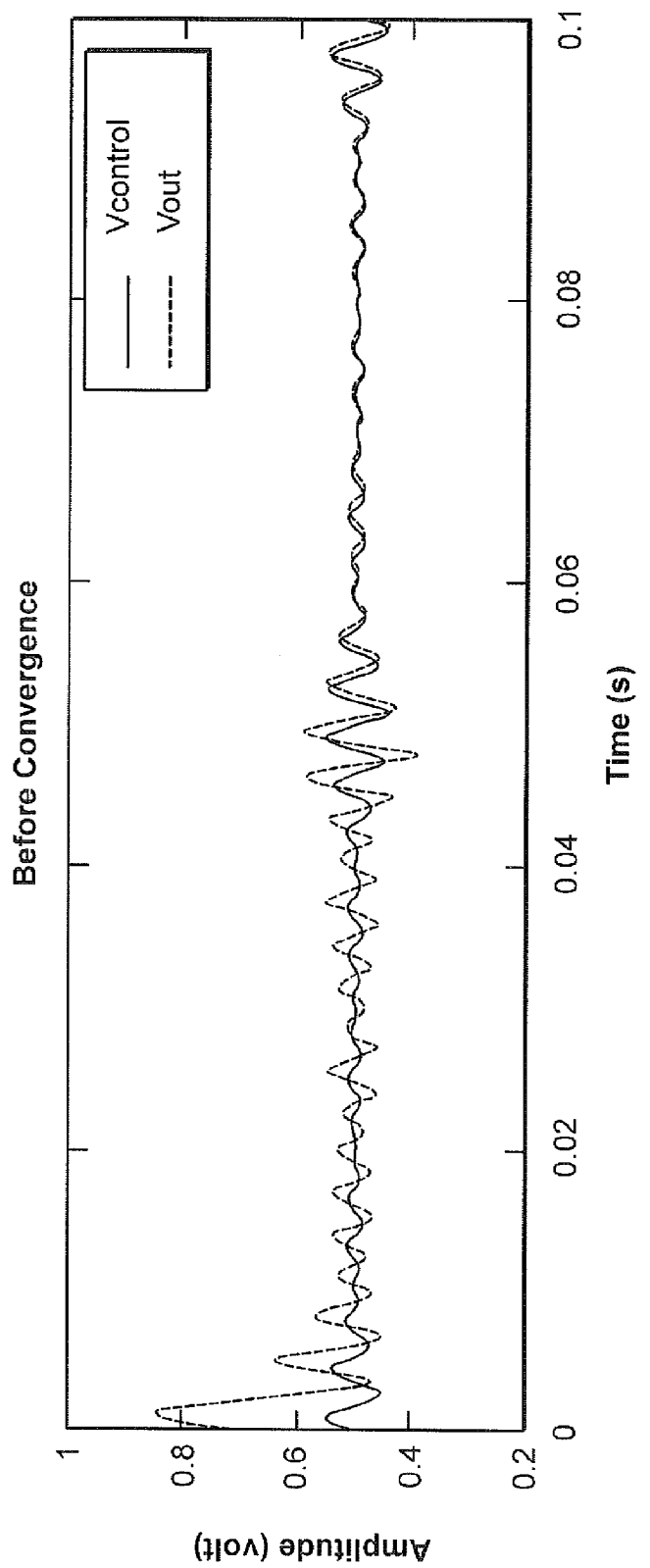
FIGS. 11A-11B are graphs illustrating learning of the inventive decoding circuit with sinusoidal inputs.
Figure 11B:
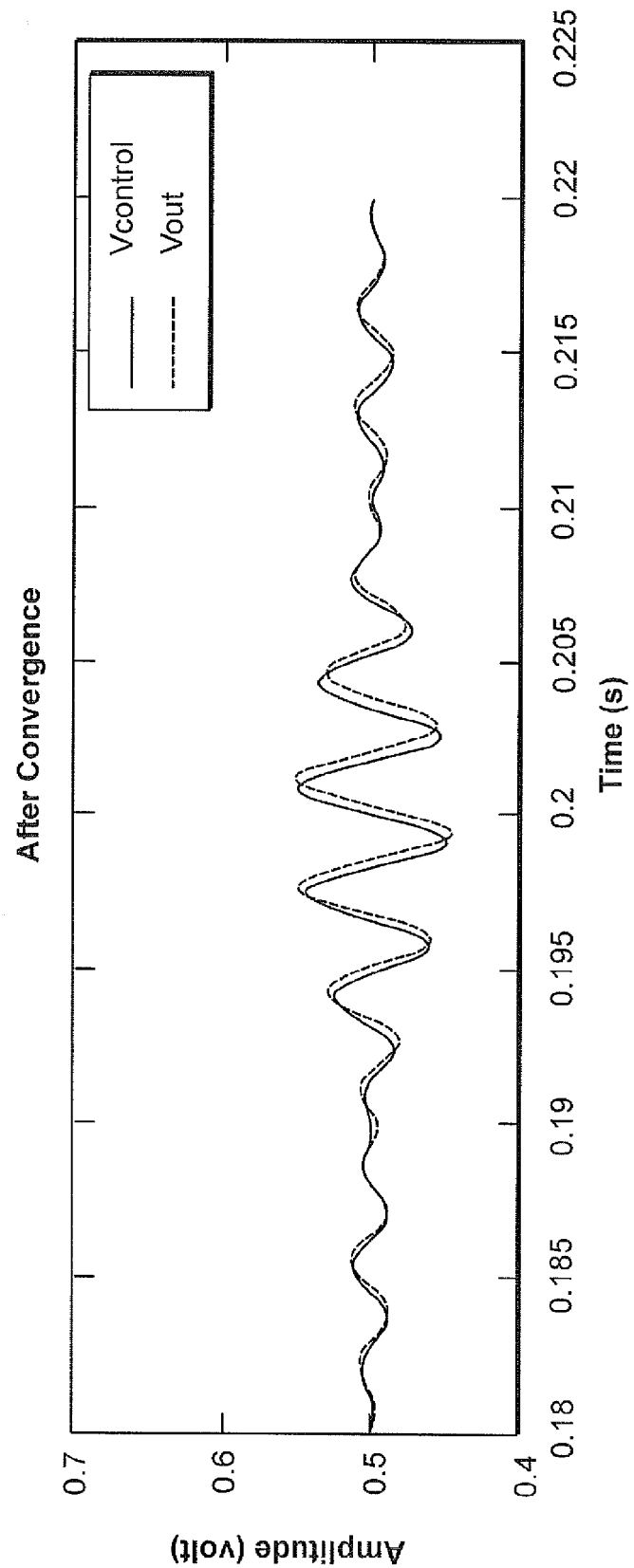

The result from this simulation is shown in FIGS. 11A-11B. The curve labeled $V_{control}$ is a motor target signal consisting of five sinusoids at the five described frequencies. The curve labeled $V_{out}$ is the output signal of our learning-and-decoding circuit. FIGS. 11A-11B shows that the output of the decoding circuit does not initially track the control input, but that good tracking is achieved after the learning process converges. There is a small difference between the motor target signal and the output of the decoding circuit after convergence. The error appears to be due to a "dead zone" in the multiplier circuit. When one of the input signals to the multiplier (e(t) for example) is very small, the output current of the multiplier does not generate a current with magnitude sufficient to change the capacitor voltage at its output.

The data used in this simulation consisted of spike times recorded on 10 channels in a memory period during which a monkey was planning a reaching arm movement in one of several allowed directions, e.g., D1 or D2, in an x-y plane. The data used in our simulation were collected from many reach trials. We mapped the motor output change due to these directional changes into an output voltage range compatible with our circuit's operation (0.5V-1V).

Using a spike-time to mean-firing-rate conversion scheme shown in FIG. 9, we first obtained mean firing rate inputs for each of our 10 channels. We attempted to learn the ten gains necessary in each channel's tunable decoding filter to correctly predict the motor output corresponding to the monkey's intended reach direction from its vector pattern of input firing rates. Time-constant tuning was not needed since instantaneous firing rates were predictive of the motor output in this case.

Figure 12:
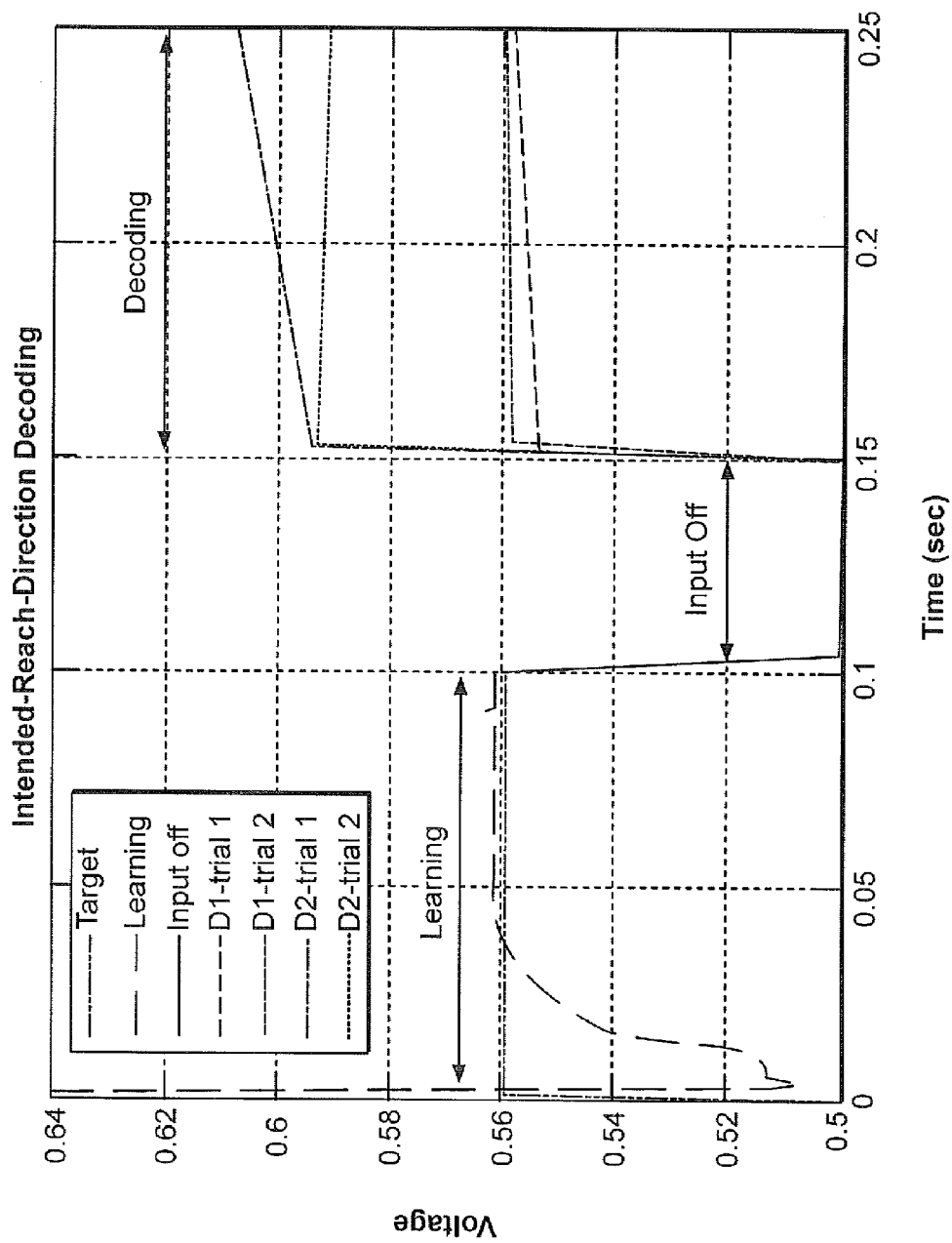
FIG. 12 is a graph illustrating learning and decoding performance of the inventive circuit with spike-time data.

FIG. 12 shows the output of our circuit during three phases; a phase of learning, a phase when the input is off, and a decoding phase. In the learning phase [0,0.1], a target output of 0.56 V is applied and the input pattern of firing rates corresponds to the monkey intending to reach in a direction D1. The circuit starts out at 0.64 V and then learns to correctly produce an output of 0.56 V during this applied pattern and track the target as shown. When the learning ends at 0.1 second, the circuit stores its learned gains. In the second phase [0.1,0.15], when all inputs are off (at 0.5 V), the circuit produces a zero output (0.5 V). In the decoding phase [0.15,0.25], when two slightly different input patterns corresponding to the monkey intending to reach for D1 (trial 1 and trial 2) are applied as inputs to the circuit, it correctly outputs voltages near 0.56 V indicating that the learned values have been properly stored. When two slightly different input patterns corresponding to the monkey intending to reach for a different direction D2 are applied (trial 1 and trial 2), the circuit now consistently produces a different output voltage near 0.6 V indicating that it is discriminating between the two input patterns.

The invention presents a novel analog learning and decoding architecture suitable for linear decoding in neuromotor prosthetics. We also presented a proof-of-concept circuit design that implemented the architecture, and that was able to learn from artificial and monkey data in simulations. The estimated power consumption of the entire system for 3 motor outputs and 100 input channels each is approximately 17 μW. Thus, the learning-and-decoding analog architecture appears to be promising for neuromotor prosthetics due to its potential for significant data reduction, the benefits of power reduction in digitization, telemetry, and post processing due to this data reduction, and because it can achieve such reductions while operating in a very energy-efficient fashion itself.

Although the present invention has been shown and described with respect to several preferred embodiments thereof, various changes, omissions and additions to the form and detail thereof, may be made therein, without departing from the spirit and scope of the invention.

What is claimed is:

1. A microchip performing a neural decoding algorithm, said microchip implemented using ultra-low power electronics comprises:
    a tunable neural decodable filter implemented using a plurality of amplifiers;
    a plurality of parameter learning filters;
    a multiplier, wherein linear capacitors at the output of said multiplier integrate output currents to form voltage signals which are used to set bias voltages through gain and time-constant biasing circuits, wherein said bias voltages set the gain and time constant of said tunable neural decodable filter; and
    analog memory,
    wherein said microchip, in a training mode, learns to perform an optimized translation of a raw neural signal received from a population of cortical neurons into motor control parameters, said optimized translation being based on a modified gradient descent least square algorithm wherein update for a given parameter in a filter is proportional to an averaged product of an error in the final output that the filter affects and a filtered version of its input; and said microchip, in operational mode, issues commands to control a device using learned mappings.

2. The microchip of claim 1, wherein said device comprises a prosthesis or a computer interface.

3. The microchip of claim 1, wherein said microchip is used in conjunction with a neuromotor prosthetic system.

4. The microchip of claim 1, wherein said optimized translation is performed according to the following learning rule:

$$-(\nabla E_i)_{f,k} = -\int_{t-\sigma}^{t} [e_i(u)] \times \left(-\frac{\partial W_f(u)}{\partial p_{f,k}} * N_f(u)\right) du,$$

where $\nabla E_i$ is a gradient, $e_i(u)$ is the error at time u, $N_f(u)$ is an N-dimensional vector containing neural signal data at time u, $W_f(u)$ is an impulse response kernel corresponding to a filter applied to $N_f(u)$, and $$\frac{\partial W_f(u)}{\partial p_{f,k}}$$

is a convolution kernel.

5. The microchip of claim 1, wherein said microchip is implantable in the brain.

6. A microchip implantable inside a skull, said microchip, in a training mode, learns to perform an optimized translation of a raw neural signal received from a population of cortical neurons in the brain positioned in said skull into motor control parameters, said optimized translation is performed according to the following learning rule:

$$-(\nabla E_i)_{f,k} = -\int_{t-\sigma}^{t} 2[e_i(u)] \times \left(-\frac{\partial W_f(u)}{\partial p_{f,k}} * N_f(u)\right) du,$$

where $\nabla E_i$ is a gradient, $e_i(u)$ is the error at time u, $N_f(u)$ is an N-dimensional vector containing neural signal data at time u, $W_f(u)$ is an impulse response kernel corresponding to a filter applied to $N_f(u)$, and $$\frac{\partial W_f(u)}{\partial p_{f,k}}$$

is a convolution kernel, said microchip, in an operational mode, issues commands to control a prosthesis using learned mappings.

7. The microchip of claim 6, wherein said microchip is used in conjunction with a neuromotor prosthetic system.

* * * * *